United States Patent [19]

McWhorter

[11] 4,200,112
[45] Apr. 29, 1980

[54] DEVICE FOR MEASURING THE FORCE OF A URINE DISCHARGE

[75] Inventor: Daniel M. McWhorter, Lake Bluff, Ill.

[73] Assignee: The Kendall Company, Boston, Mass.

[21] Appl. No.: 923,860

[22] Filed: Jul. 12, 1978

[51] Int. Cl.² ........................ G01F 1/00; G01F 23/00
[52] U.S. Cl. .................................... 128/761; 128/771
[58] Field of Search ............... 128/761, 762, 763, 747, 128/768, 771, 760; 73/215, 194 R, 194 M, 428, 700, 709, 425.4

[56] References Cited

U.S. PATENT DOCUMENTS

| 1,508,017 | 9/1924 | Greve | 73/215 |
|---|---|---|---|
| 1,621,354 | 3/1927 | Dawley | 73/215 |
| 1,834,392 | 12/1931 | Fechheimer | 73/212 |
| 2,101,165 | 12/1937 | Cole et al. | 73/212 |
| 2,212,186 | 8/1940 | Ricardo et al. | 73/205 |
| 3,122,924 | 3/1964 | Pall | 73/401 |
| 3,541,858 | 11/1970 | Bonczek | 73/747 |
| 3,831,446 | 8/1974 | Dye | 73/194 R |
| 3,859,854 | 1/1975 | Dye et al. | 73/215 |
| 3,871,230 | 3/1975 | Dye et al. | 73/215 |
| 3,871,231 | 3/1975 | Ciarico | 73/215 |
| 3,884,072 | 5/1975 | Cheng | 73/215 |
| 3,929,412 | 12/1975 | Villari | 73/259 |
| 4,085,616 | 4/1978 | Patel et al. | 128/771 |

*Primary Examiner*—Willis Little
*Attorney, Agent, or Firm*—Powell L. Sprunger

[57] ABSTRACT

A device for measuring a urine discharge comprising, a hollow receptacle having an inlet port adjacent an upper end of the receptacle to receive the urine discharge and a channel below the inlet port to receive the liquid passing through the port. The device measures the force of the discharge intermediate the port and channel.

10 Claims, 5 Drawing Figures

DEVICE FOR MEASURING THE FORCE OF A URINE DISCHARGE

BACKGROUND OF THE INVENTION

The present invention relates to a device for measuring a discharge of urine.

In the past, it has been found desirable to obtain various data pertaining to a urine discharge. In particular, it was discovered that many urological problems could be readily diagnosed by analyzing information obtained during the natural voiding of urine by patients. For example, the capability of a patient to rapidly void a large volume of urine indicates an absence of a urethral stricture in the patient. If the cast distance or force of the urine discharge is relatively low in spite of a normal voiding volume per unit time, this condition of the patient suggests inadequate contraction of the patient's bladder, rather than a urethral obstruction. Presently, various types of devices are utilized to obtain data on the urine stream, but many of such devices have suffered from less than total reliability because they have required the presence of one or more observers while the patient is voiding. It is obvious that administration of such devices in this manner creates sufficient psychological difficulties for many of the patients to effect voiding. Consequently, if the patients void at all, the potentially erroneous data obtained may result in a false diagnosis and a loss of confidence in the device by the physician. A further complication arises from the fact that many of these devices are rather bulky, and somewhat difficult to use.

SUMMARY OF THE INVENTION

A principal feature of the present invention is the provision of a device of simplified construction for measuring a discharge of urine, and which may be self-administered by a patient.

The device of the present invention comprises, a hollow receptacle having an enlarged portion defining an inlet port and a cavity communicating with the port, and channel means communicating with the cavity below the port to receive the discharge passing through the port and cavity. The device has a U-shaped tube defining a lumen and having first and second generally aligned upright arms connected by a lower arcuate portion of the tube. The first arm is substantially shorter in length than the second arm and is positioned in the cavity with the first arm defining an opening facing toward the port. The second arm extends upwardly along a wall of the enlarged portion, and the device has means for indicating the maximum height of urine attained in the lumen of the second arm.

A feature of the present invention is that a portion of the discharge passes through the tube opening and into the lumen of the second arm, while the remainder of the discharge passes around the tube into the channel means.

Another feature of the invention is that the height of liquid in the lumen of the second arm above the opening in the first arm provides an indication of the force of the urine discharge.

Still another feature of the invention is that the indicating means determines the maximum height of urine attained above the second arm opening, and thus provides an indication of the maximum force of the urine discharge.

Still another feature of the invention is that the remainder of the discharge passing into the channel means may be utilized to determine additional data associated with the discharge, such as peak flow rate and volume.

Further features will become more fully apparent in the following description of the embodiments of this invention and from the appended claims.

DESCRIPTION OF THE PREFERRED EMBODIMENTS

Figure 1:
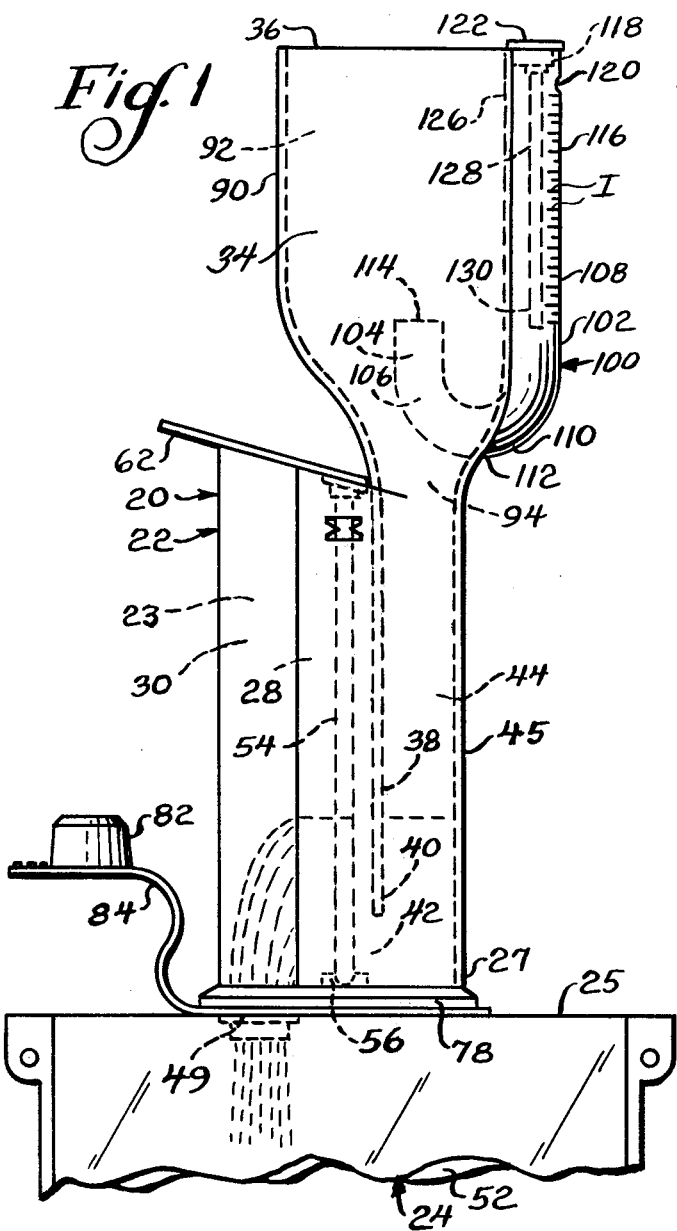
FIG. 1 is a fragmentary elevational view of a liquid measuring device including a force measuring apparatus according to the present invention.

Referring now to FIGS. 1-5, there is shown a device generally designated 20 for measuring and collecting a discharge of liquid, such as urine. The device 20 includes a hollow receptacle designated generally 22 having a cavity 23, and a container designated generally 24 having an upper end 25 releasably attached to a lower end 27 of the receptacle 22. Preferably, the receptacle 22 is made from a suitable transparent material, such as plastic.

The receptacle 22, which has rounded end portions and an elongated central portion, has an upright wall 26 which extends laterally across the inside of the receptacle and which extends vertically substantially the height of the receptacle. The upright wall 26 separates the inside of the receptacle into a compartment 28 and a passageway or channel 30. The lower end of the compartment 28 is closed by a bottom wall 31, while the upper end of the passageway 30 and compartment 28 is partially covered by an upper wall 32.

Figure 5:
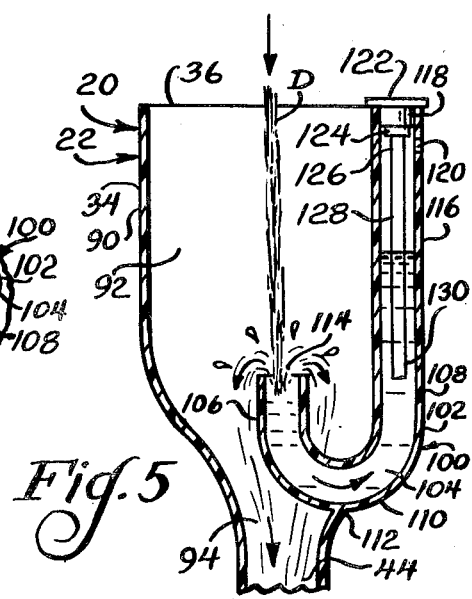
FIG. 5 is a sectional view of an upper portion of the device illustrating use of the apparatus to measure the force of a urine discharge.

The receptacle 22 has an enlarged portion 34 adjacent the upper end of the receptacle defining an inlet port or opening means 36 to receive the incoming urine discharge, as indicated by the direction of the arrow in FIG. 5. The receptacle has a wall 38 extending laterally across the inside of the receptacle, and having a lower end 40 defining a space 42 intermediate the lower end 40 of the wall 38 and the lower or the bottom wall 31 of the receptacle. The wall 38 partially defines the compartment 28 and a channel or channel means 44 intermediate the wall 38 and an outer side wall 45 of the receptacle 22. Thus, a major portion of the urine discharge passes from the opening means 36 through the channel means 44 and space 42 into the compartment 28.

Figure 2:
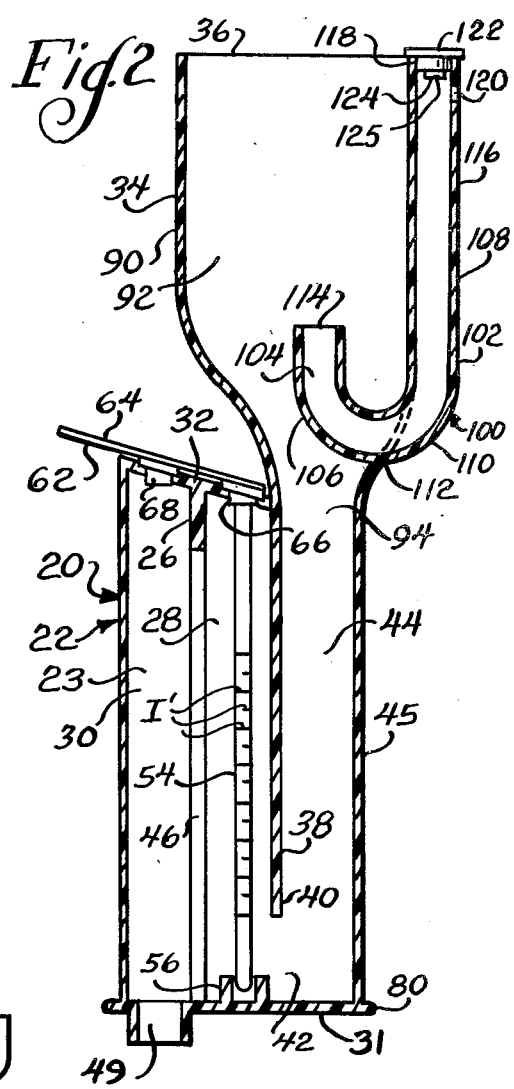
FIG. 2 is a sectional view of the device of FIG. 1.
Figure 3:
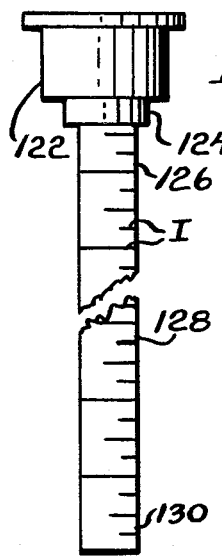
FIG. 3 is a fragmentary elevational view of an indicating strip and cap for the force measuring apparatus of FIG. 1.
Figure 3:
Figure 4:
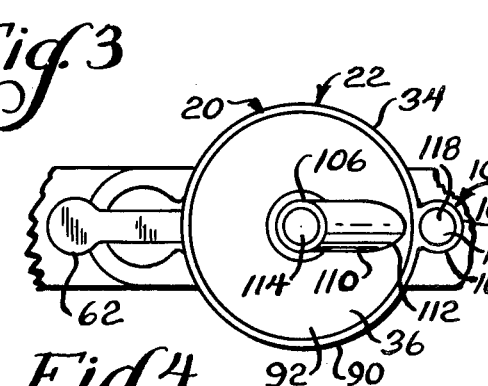
FIG. 4 is a top plan view of the device of FIG. 1.

The wall 26 has an elongated vertical slot or opening means 46 communicating between the compartment 28 and the passageway means 30 to permit passage of the liquid from the compartment to the passageway means and through an outlet port 49 into a chamber 52 in the container 24. As shown in FIGS. 1 and 2, an indicating strip 54 is removably inserted into the compartment 28, with retaining means 56 adjacent the lower end 27 of the receptacle releasably receiving a lower end of the indicating strip 54. The retaining means 56 has a pair of bosses extending from the bottom wall 31 into the cavity 23, with the bosses defining a slot which receives the lower end of the strip 54 and assists in retaining the strip 54 in an upright position in the compartment 28.

As shown in FIG. 2, a retaining member 62 has an elongated flexible tab 64 having first and second spaced plugs 66 and 68, respectively, extending outwardly from one surface of the tab 64, with the first plug 66 being located adjacent one end of the tab 64, and the other plug 68 being located intermediate the plug 66 and the other end of the tab. The first plug 66 has a slot to receive and retain an upper end of the indicating strip 54. The upper wall 32 has a first opening communicating with the compartment 28 to receive the indicating strip 54 and first plug 66, with the first opening having dimensions to snugly engage the first plug 66. The upper wall 32 also has a second opening extending through the wall to snugly receive the second plug 68. Thus, the first and second plugs 66 and 68 are removably received in the first and second openings to releasably retain the tab 64 in place above the upper wall 32, while the first plug 66 assists in retaining the upper end of the indicating strip 54 in an upright position in the compartment 28. As shown in FIGS. 1 and 2, the outer end of the tab 64 extends past the enlarged portion 34 to facilitate removal of the retaining member 62 from the receptacle 22.

The indicating strip 54 is sensitive to contact or wetting by liquid, such as urine, and provides an indication of the maximum height of liquid reached in the compartment 28 during the liquid discharge. Any suitable material may be utilized for the indicating strip 54, such as a material which changes color upon contact by the liquid. For example, a methylene blue compound or rhodamine may be utilized on the strip 54 to obtain the color contrast desired. Preferably, the indicating strip 54 is utilized a single time to measure the height of liquid in the compartment 28. Thus, the retaining member 62 permits easy placement and removal of indicating strips 54 in the receptacle 22. After removal of the strip, flow rate information may be determined by suitable indicia I' spaced along the strip. If desired, the strip 54 may be discarded after it has been removed and the information determined. Alternatively, if it is desired to keep the strip for a later reading, the other end of the tab 64 may be placed in a clip (not shown), or the second plug 68 may be positioned in an opening of a retaining device (not shown) to retain the strip until it is read. In either event, the retaining member 62 permits handling of the strip 54 in an sanitary manner without contacting the strip with the user's hands.

As shown in FIGS. 1 and 2, the container 24 has an upper resilient support member 78 which is releasably attached to a flange 80 at the lower end 27 of the receptacle 22. The support member 78 also includes a closure plug 82 attached to the support member 78 by a strap 84. The plug 82 is removably received in an opening of the support member 78 when the container 24 is removed from the receptacle 22. As shown, the container 24 has a pair of flexible side walls depending from the support member 78 and defining the chamber 52. The container side walls may be made of any suitable material, preferably transparent, such as polyethylene, and one of the side walls may have a plurality of vertically spaced indicia to measure the volume of liquid collected in the chamber 52.

With reference to FIGS. 1–5, the enlarged portion 34 of the receptacle has a side wall 90 which defines a cavity 92 communicating between the inlet port 36 and an opening 94 adjacent an upper end of the channel 44. Thus, the side wall 90 of the enlarged portion 34 directs the incoming urine discharge D from the port 36 toward the opening 94 and a lower part of the receptacle.

The device 20 also has a force measuring apparatus generally designated 100 comprising a U-shaped tube 102 defining a lumen 104. The tube 102 has a first upright arm 106, a second elongated upright arm 108, and a lower arcuate portion 110 connecting the first and second arms 106 and 108. As shown, the second arm 108 has a substantially greater length than the first arm 106, and the arcuate portion 110 of the tube 102 extends through an opening 112 in a back part of the side wall 90, such that the lumen of the second arm extends upwardly along the side wall 90. In this configuration, the first arm 106 is located in the receptacle cavity 92 with an opening 114, defined by an upper end of the first arm 106 and communicating with the lumen 104, facing towards the receptacle port 36. An upper segment 116 of the second arm 108 extending above the first arm opening 114 defines an aperture 118 at the upper end of the second arm communicating with the lumen in the second arm 108. Further, the second arm segment 116 may have a vent 120 in the wall of the segment communicating between the lumen 104 and the atmosphere adjacent an upper end of the segment, as shown.

The apparatus 100 may have a cap 122 of suitable material which is snugly received in the aperture 118 to selectively close the upper end of the lumen 104 in the second arm 108. The cap 122 may have a depending flange 124 defining a slot 125 to receive and support the upper end 126 of a second indicating strip 128, which may be constructed in a manner as previously described with the first indicating strip 54. As best shown in FIG. 5, the indicating strip 128 has lateral dimensions less than the inner diameter of the lumen 104 in the second arm 108, and the strip 128 preferably has a length such that a lower end 130 of the strip 128 is located at the vertical level of the first arm opening 114, i.e., the length of the strip 128 is approximately equal to the height of the second arm segment 116 between the first arm opening 114 and the placed cap 122. Thus, the cap 122 supports the second strip 128 in the lumen 104 of the second arm 108 at a location for recording the maximum height of urine attained in the lumen of the second arm 108 above the first arm opening 114. The indicating strip 128 and the outer wall of the second arm segment 116 may have suitably calibrated indicia I for a purpose which will be described below.

In use of the device, the plug 82 of the container 24 is removed from the opening of the support member 78, and the support member 78 of the container is attached to the lower end 27 of the receptacle 22. The port 36 of the receptacle 22 is then positioned by a patient in privacy to receive the discharge of urine D. With reference to FIG. 5, as the liquid discharge D passes into the enlarged portion 34 of the receptacle 22 through the port, a portion of the discharge D passes through the first arm opening 114 into the lumen 104 of the tube 102 and into the second arm 108. Due to the force of the incoming discharge D, the height of urine in the lumen of the second arm 108 rises to a level above the opening 114 of the first arm 106, with the height of liquid in the second arm above the opening 114 providing an indication of the discharge force. Thus, the indicia I on the indicating strip 128 and the second arm segment 116 may be calibrated to provide an indication of the instantaneous discharge force. In addition, the indicating strip 128 permanently records the maximum height of urine reached in the second arm 108 above the first arm opening 114, such that the indicating strip 128 indicates the maximum discharge force upon completion of voiding. Hence, the maximum force may be determined by the strip 128 even though the device is self-administered by the patient in privacy.

Both before and after the maximum height of urine is attained in the second arm 108, a major portion of the discharge D passes around the opening 114 of the first arm 106 into a lower part of the receptacle 22. Thus, a major portion of the liquid passes through the opening 94 and channel 44, and collects in a lower part of the compartment 28, after which it passes from the compartment 28 through the slot 46 into the passageway 30. From the passageway 30, the liquid flows through the outlet port 49 into the chamber 52 of the container 24 for collection therein.

As the rate of discharge into the receptacle 22 increases, the height of liquid in the compartment 28 also increases while the liquid also drains through the slot 46 into the passageway 30. For a given rate of flow of the discharge into the receptacle the liquid attains a fixed height in the compartment, while the liquid passes at a fixed predetermined rate of flow through the slot 46. Hence, if the rate of flow of the liquid discharge into the receptacle is greater than the predetermined exit rate, the height of liquid in the compartment increases. As long as the rate of flow of the discharge into the receptacle continues to increase, the height of liquid in the compartment 28 continues to rise, and the rate of flow of liquid through the slot 46 also increases. When the flow rate of the incoming discharge abates, the liquid drains from the compartment 28 into the passageway 30 faster than it enters the compartment, and the height of the liquid in the compartment begins to subside.

Peak flow rate of the incoming liquid discharge may be defined as the maximum rate of flow of the discharge. Since the height of liquid in the compartment raises or lowers responsive to an increase or decrease, respectively, of the flow rate of the incoming discharge, it is apparent that the maximum height of liquid attained in the compartment during the discharge serves as an indication of the approximate peak flow rate of the discharge. Although anomalies in the discharge, such as a momentary surge of the discharge, may not be ultimately reflected in the maximum liquid height in the compartment, due, in part to the lag between the time the discharge enters the receptacle and the time it enters the compartment, the device determines the peak flow rate with sufficient accuracy for such purposes as are under discussion. In particular, a urine stream during voiding has a relatively slow rate of change of flow rate, and the device of the present invention indicates a peak flow rate for the discharge which is sufficiently accurate for purposes of diagnosing the patient.

It is possible that the approximate peak flow rate of the urine discharge may be determined by observing the highest level of liquid accumulated in the compartment 28 during the discharge. As in the case of the force apparatus 100, direct reading by the patient may be impractical or difficult during self-administration of the apparatus. Accordingly, the indicating strip 54 has been provided to automatically record the approximate maximum height of liquid collected in the compartment 28 during the liquid discharge. After the liquid discharge has been completed, a direct reading of the approximate peak flow rate may be determined by the indicia I', either before or after removal of the indicating strip 54 from the receptacle 22. Alternatively, the indicia I' may be placed on the wall of a transparent receptacle 22.

It is apparent that the rate of drainage from the compartment 28 into the passageway 30 is partly dependent upon the precise structure of the receptacle 22. For example, although the slot 46 is shown as having parallel sides, it is contemplated that the slot may be widened or narrowed at desired vertical positions to increase or decrease the flow rate of liquid through the wall in that area, and the wall 26 may have a plurality of slots or openings if desired. Also, the cross sectional area of the compartment 28 itself may be selected of a suitable size to provide the desired sensitivity of liquid column height for a more accurate determination of the peak flow rate.

It is contemplated that a particular structure for the receptacle would first be established, dependent on the accuracy desired and the expected range of values for the peak flow rate of the liquid discharge. Next, the receptacle could be calibrated against known constant flow rates of a discharge passing into the receptacle to determine the appropriate location of the indicia I' on the strip. That this may be readily accomplished is apparent from the fact that the peak flow rate for a discharge having a constant flow rate is the value of the constant flow rate itself. Accordingly, when the discharge of constant flow rate is directed into the receptacle, liquid rises in the compartment to a level at which entering the compartment is offset by the liquid draining from the compartment into the channel, and the receptacle or strip is marked at this height for peak flow rate by the value of the flow rate of the constant discharge. The force measuring apparatus 100 may be calibrated against known forces in a similar manner.

As noted above, once the rate of flow of the liquid discharge into the receptacle abates, the height of the liquid in the compartment 28 subsides, and the approximate peak flow rate has already been determined on the indicating means or strip 54. During the remainder of the liquid discharge, the liquid continues to drain from the compartment 28 into the passageway 30 until the discharge is terminated and drainage from the compartment 28 to the channel 30 eventually stops. Since the liquid drains from the passageway 30 of the receptacle 22 into the container 24, the approximate volume of liquid which collects in the container 24 during the liquid discharge may be readily determined by the indicia on the container 24.

Since the patient may use the device without observation, unnatural voiding or failure to void which may occur when a patient voids under observation is prevented. After voiding, the patient merely summons the physician or nurse, who then uses the device to diagnose the patient's voiding. The indicating strips 128 and 54 may be removed from the receptacle 22 to obtain a reading of the maximum force and peak flow rate of the urine discharge through use of the indicia I and I' on the respective strips. The container 24 may be removed from the receptacle 22 to obtain a specimen of urine from the chamber 52 of the container through the container opening. Alternatively, the closure plug 82 may be placed in the opening to close the opening and cavity 52 of the container 24, and the specimen may be retained for later use, if desired. In either event, the closed container 24 may be discarded in a sanitary manner after removal from the receptacle 22. Although the device is intended for disposable use, the receptacle 22 may be cleaned and sterilized for future use with different indicating strips 128 and 54 in order to reduce the cost of diagnosing various patients.

Thus, in accordance with the invention, the maximum force of the discharge may be readily determined by the indicia I on the strip 128, and the peak flow rate of the discharge may be determined by the indicating strip 54. Further, the total volume of the discharge collected in the chamber 52 of the container 24 may be determined through use of suitable indicia on the sidewalls of the container 24. The data associated with the maximum force, peak flow rate, and volume of the discharge may then be utilized to diagnose the patient. For example, the capability of the patient to rapidly void a large volume of urine indicates the absence of a possible obstruction in the urethra. However, if the cast distance or force of the urine discharge is relatively low in spite of a normal voiding volume per unit time, this condition in the patient suggests inadequate contraction of the patient's bladder, rather than an obstruction in the urethra. In this manner, the data may be utilized to screen patients for possible urological problems, and to further determine the source of such difficulties, if present.

The foregoing detailed description is given for clearness of understanding only, and no unnecessary limitations should be understood therefrom, as modifications will be obvious to those skilled in the art.

I claim:

1. A device for measuring a urine discharge, comprising: a hollow receptacle having an inlet port adjacent an upper end of the receptacle to receive the urine discharge and channel means below the inlet port to receive the discharge passing through the port, a U-shaped tube defining a lumen and having first and second upright arms, said first arm being shorter in length than the second arm and defining an opening facing toward said port such that a portion of said discharge passes into the tube opening and lumen to provide an indication of the discharge force in the second arm associated with the height of urine attained in the lumen of the second arm, and vent means disposed in said second arm for venting the upper portion of said second arm.

2. The device of claim 1 including indicating means associated with said second arm for determining the maximum height of urine attained in the lumen of the second arm.

3. The device of claim 1 including indicating means associated with said second arm for determining the maximum height of urine attained in the lumen of the second arm above the first arm opening.

4. The device of claim 1 including means insertable in the upper end of said second arm to effect the closing thereof.

5. The device of claim 1 including a wettable indicating strip positioned in the lumen of said second arm.

6. The device of claim 1 wherein an upper end of the second arm includes an aperture communicating with the tube lumen, and including a cap removably positioned in said aperture to close the lumen of said second arm.

7. The device of claim 6 including an elongated indicating strip positioned in the lumen of the second arm.

8. The device of claim 7 wherein said cap includes means for supporting said strip in said lumen.

9. The device of claim 8 wherein said strip has a length approximately equal to the height between said first arm opening and the cap when positioned in said aperture.

10. A device for measuring a urine discharge, comprising: a hollow receptacle having an enlarged portion defining an inlet port and a cavity communicating with the port, and channel means communicating with the cavity below said port to receive the discharge passing through the port and cavity, a U-shaped tube defining a lumen and having first and second generally aligned upright arms connected by a lower arcuate portion of said tube, said first arm being substantially shorter in length than the second arm and being positioned in said cavity, with the first arm defining an opening facing toward said port to receive a portion of said discharge, and with said second arm extending upwardly along a wall of said enlarged portion, vent means disposed in said second arm for venting the upper portion of said second arm, and indicating means associated with the height of urine attained in the lumen of the second arm for indicating the maximum height of urine attained in the lumen of said second arm.

* * * * *